United States Patent
Wong et al.

(10) Patent No.: US 11,521,750 B1
(45) Date of Patent: Dec. 6, 2022

(54) COMPUTERIZED SYSTEM FOR AUTOMATED GENERATION OF ORDERED OPERATION SET

(71) Applicant: Express Scripts Strategic Development, Inc., St. Louis, MO (US)

(72) Inventors: Mark D. Wong, Chesterfield, MO (US); Amit K. Bothra, St. Louis, MO (US); Pritesh J. Shah, Paramus, NJ (US); Karnik D. Patel, Hillsborough, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 190 days.

(21) Appl. No.: 16/930,822

(22) Filed: Jul. 16, 2020

Related U.S. Application Data

(60) Provisional application No. 62/874,675, filed on Jul. 16, 2019.

(51) Int. Cl.
*G16H 50/30* (2018.01)
*G16H 10/60* (2018.01)
*G16H 20/10* (2018.01)

(52) U.S. Cl.
CPC ............ *G16H 50/30* (2018.01); *G16H 10/60* (2018.01); *G16H 20/10* (2018.01)

(58) Field of Classification Search
CPC ......... G16H 50/30; G16H 10/60; G16H 20/10
See application file for complete search history.

(56) References Cited

U.S. PATENT DOCUMENTS

| | | | |
|---|---|---|---|
| 2013/0226608 A1* | 8/2013 | Di Lascia | G16H 20/70 705/2 |
| 2017/0154166 A1 | 6/2017 | Klein | |
| 2017/0169397 A1 | 6/2017 | Castelli | |
| 2017/0220758 A1 | 8/2017 | Cox | |
| 2017/0286621 A1 | 10/2017 | Cox | |
| 2017/0286995 A1 | 10/2017 | Shenk | |
| 2017/0300656 A1 | 10/2017 | Cox | |
| 2018/0075207 A1 | 3/2018 | Schmidt | |
| 2019/0371443 A1 | 12/2019 | Petricoin, III | |
| 2020/0013071 A1 | 1/2020 | Sri | |
| 2020/0118661 A1 | 4/2020 | Jordan | |

\* cited by examiner

*Primary Examiner* — Michael Tomaszewski
*Assistant Examiner* — Mohmad Muqueeth
(74) *Attorney, Agent, or Firm* — Miller Johnson

(57) ABSTRACT

A computerized method includes determining a clinical opportunity to improve care for a user according to automated triggering of a gap identification rule, generating a persona of the user based on one or more personalization scores that are specific to the user, and generating a care plan for reducing the gap in care based on the persona. The care plan includes a plurality of methods of increasing compliance of the user with the care plan, selected based on the one or more personalization scores, and include different modes of communicating with the user either directly or through at least one of a physician and a pharmacist depending on the one or more personalization scores. The method includes deploying the care plan to provide automated selection of one or more of the different modes of communicating with the user to increase compliance of the user with the care plan.

18 Claims, 7 Drawing Sheets

COMPUTERIZED SYSTEM FOR AUTOMATED GENERATION OF ORDERED OPERATION SET

CROSS-REFERENCE TO RELATED APPLICATIONS

This application claims the benefit of U.S. Provisional Application No. 62/874,675, filed on Jul. 16, 2019. The entire disclosure of the above application is incorporated herein by reference.

FIELD

The present disclosure relates generally to computerized healthcare systems and more particularly to computerized healthcare systems for generating personalized healthcare plans.

BACKGROUND

When a user (also referred to as a patient) is prescribed medication for a condition, successful treatment of that condition requires following the prescription schedule. In other words, the user must fill the prescription, follow the dosage instructions, and then refill the prescription as necessary. Deviating from the dosage and refill instructions is referred to as non-adherence.

According to some estimates, non-adherence results in $300 billion of medical waste every year. This medical waste may include drugs dispensed but not taken, an increase in medical practitioner visits, and, most particularly, an increase in acute episodes that are generally much more expensive to treat than to prevent.

Because of the increased cost and worse patient outcomes caused by non-adherence, providers in the medical space (including health insurers and pharmacy benefit managers) may perform interventions (also referred to as outreach) with users. These interventions may take the form of physical visits, phone calls, emails, texts, mobile alerts, etc.

However, with limited resources, frequent personal outreach to every user may not be possible. Therefore, there is a need to develop better intervention systems including personalized care plans to achieve more positive patient outcomes.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized method includes determining a clinical opportunity to improve care for a user according to automated triggering of a gap identification rule. The clinical opportunity indicates a gap in care for the user. The method includes generating a persona of the user based on one or more personalization scores that are specific to the user, and generating a care plan for reducing the gap in care based on the persona. The care plan is personalized for the user and includes a plurality of methods of increasing compliance of the user with the care plan, and the methods are selected based on the one or more personalization scores and include different modes of communicating with the user either directly or through at least one of a physician and a pharmacist depending on the one or more personalization scores. The method includes deploying the care plan to provide automated selection of one or more of the different modes of communicating with the user to increase compliance of the user with the care plan.

In other features, the one or more personalization scores include at least one of a first score indicating a risk of the user having the gap in care, a second score indicating a likelihood of the user having a positive outcome of a targeted action aimed at reducing the gap in care, a third score indicating a preferred communication channel of the user, a fourth score indicating out-of-pocket expenses of the user, a fifth score indicating an ability of a physician to reduce the gap in care, and a sixth score indicating an ability of a pharmacist to reduce the gap in care. In other features, the different modes of communicating with the user are selected according to at least three of the first score, the second score, the third score, the fourth score, the fifth score, and the sixth score.

In other features, the computerized method includes monitoring an outcome of the deployed care plan according to a success level of increased compliance of the user with the care plan, and modifying the deployed care plan according to the monitored outcome of the deployed care plan.

In other features, the gap identification rule includes at least one of an adherence rule configured to trigger when a medication on hand value of the user falls below a specified threshold, a maintenance rule configured to trigger when a prescription refill is late to fill beyond a specified delay period, and a continuance rule configured to trigger when a first prescription fill of a new prescription is late to fill beyond a specified delay period.

In other features, the different modes of communicating with the user include at least one of an email campaign, a letter campaign, an automated outbound messaging (AOM) campaign, a live call campaign, an academic detailer campaign, a medical device or monitor campaign, a rational medical campaign, a lab test kit campaign, and a member digital application campaign.

In other features, the gap in care for the user comprises a missed prescription drug refill, and the automated triggering of the gap identification rule is configured to occur in response to detection of the missed prescription drug refill by comparison to a prescription refill schedule of the user according to one or more automated rules, and different modes of communicating with the user include communicating with the user to suggest obtaining the missed prescription drug refill.

In other features, the computerized method includes determining a second clinical opportunity to improve care for a user according to automated triggering of a second gap identification rule, the second clinical opportunity indicating a second gap in care for the user. In other features, deploying the care plan includes automated selection of one or more of the different modes of communicating with the user according to both of the triggered gap identification rules, to increase compliance of the user with both of the gaps in care for the user. In other features, deploying the care plan includes determining which of the triggered gap identification rules has a highest priority, and automatically selecting one or more of the different modes of communicating with the user according to the triggered gap identification rule having the highest priority.

In other features, the different modes of communicating with the user each have a different priority level. The method includes communicating with the user according to a mode of communication having a highest priority level, determining whether the highest priority level of communication resulted in a successful outcome, and in response to a determination that the mode of communication having the highest priority level did not have a successful outcome, automatically communicating with the user according to a mode of communication having a second highest priority level.

In other features, a computer system includes memory configured to store computer-executable instructions, at least one gap identification rule, and a personalization database including one more personalization scores that are specific to a user. The system includes at least one processor configured to execute the instructions. The instructions include determining a clinical opportunity to improve care for the user according to automated triggering of the gap identification rule. The clinical opportunity indicates a gap in care for the user. The instructions include generating a persona of the user based on the one or more personalization scores that are specific to the user, and generating a care plan for reducing the gap in care based on the persona. The care plan is personalized for the user and comprises a plurality of methods of increasing compliance of the user with the care plan. The methods are selected based on the one or more personalization scores and include different modes of communicating with the user either directly or through at least one of a physician and a pharmacist depending on the one or more personalization scores. The method includes deploying the care plan to provide automated selection of one or more of the different modes of communicating with the user to increase compliance of the user with the care plan.

In other features, the one or more personalization scores include at least one of a first score indicating a risk of the user having the gap in care, a second score indicating a likelihood of the user having a positive outcome of a targeted action aimed at reducing the gap in care, a third score indicating a preferred communication channel of the user, a fourth score indicating out-of-pocket expenses of the user, a fifth score indicating an ability of a physician to reduce the gap in care, and a sixth score indicating an ability of a pharmacist to reduce the gap in care. In other features, the different modes of communicating with the user are selected according to at least three of the first score, the second score, the third score, the fourth score, the fifth score, and the sixth score.

In other features, the instructions include monitoring an outcome of the deployed care plan according to a success level of increased compliance of the user with the care plan, and modifying the deployed care plan according to the monitored outcome of the deployed care plan. In other features, the gap identification rule includes at least one of an adherence rule configured to trigger when a medication on hand value of the user falls below a specified threshold, a maintenance rule configured to trigger when a prescription refill is late to fill beyond a specified delay period, and a continuance rule configured to trigger when a first prescription fill of a new prescription is late to fill beyond a specified delay period.

In other features, the different modes of communicating with the user include at least one of an email campaign, a letter campaign, an automated outbound messaging (AOM) campaign, a live call campaign, an academic detailer campaign, a medical device or monitor campaign, a rational medical campaign, a lab test kit campaign, and a member digital application campaign.

In other features, the instructions include determining a second clinical opportunity to improve care for a user according to automated triggering of a second gap identification rule, wherein the second clinical opportunity indicates a second gap in care for the user. In other features, deploying the care plan includes determining which of the triggered gap identification rules has a highest priority, and automatically selecting one or more of the different modes of communicating with the user according to the triggered gap identification rule having the highest priority.

In other features, the different modes of communicating with the user each have a different priority level. The instructions include communicating with the user according to a mode of communication having a highest priority level, determining whether the highest priority level of communication resulted in a successful outcome, and in response to a determination that the mode of communication having the highest priority level did not have a successful outcome, automatically communicating with the user according to a mode of communication having a second highest priority level.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Figure 1:
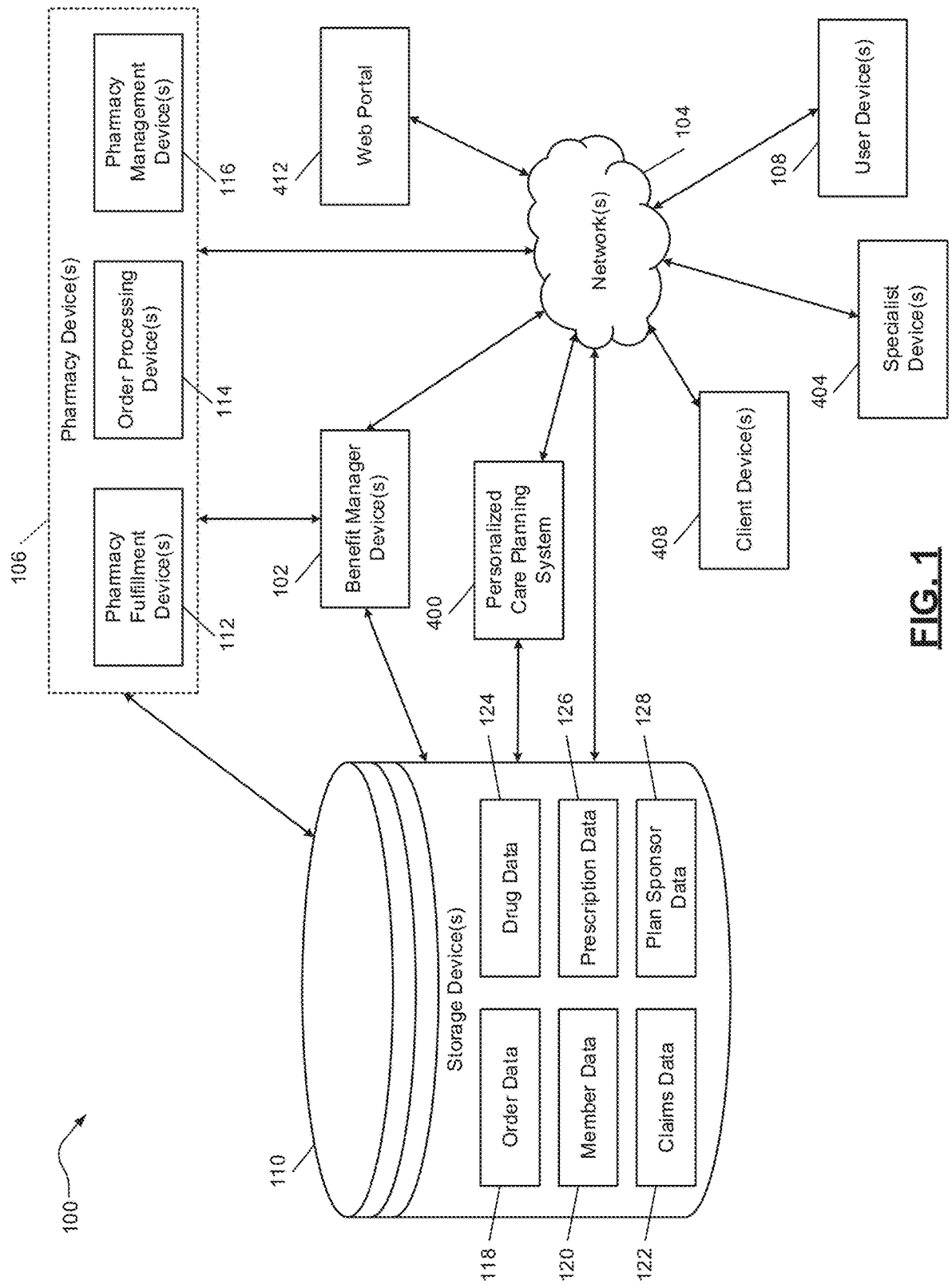
FIG. 1 is a functional block diagram of an example system including a high-volume pharmacy.

The present disclosure relates to personalizing care for members to ensure that the right member gets the right intervention at the right time to meet outcome-based goals of a healthcare system. The care coordination can be further improved by interconnecting other stakeholders such as physicians, pharmacies, and other vendors of the healthcare system so that the stakeholders can remain aligned with the members' healthcare needs and can help meet the outcome-based goals.

In some systems, an operator in the medical space can use an intervention system to identify users for whom interventions are necessary and to select the appropriate interventions for specific users. Interventions may be warranted when it appears likely that there will be a gap in care, such as a medication running out prior to conclusion of a treatment regimen. In one specific example, a gap in care is experienced when a user exhausts their supply of pills prior to obtaining a refill of the prescription.

Interventions may take the form of an operator in the medical space (such as a health insurer or a pharmacy benefit manager) contacting the user. For example, an operator may directly contact the user or request that a local pharmacy, medical provider, or caregiver contact the user. These contacts may take the form of personal visits, telephone calls, text messages, mobile alerts, emails, postal letters, etc. Communications with the user may include reminders about their course of treatment, including expected dates by which existing medication will be exhausted, expired, or otherwise need refilling.

The communications may also include warnings about the potential effects of a gap in care. The communications may provide incentives for the user to avoid a gap in care, such as discounts on drugs, free shipping, or discounts on expedited shipping. In addition, the communications may assist the user in setting up automatic refills and other technological approaches to increasing adherence. Another technological approach to increase adherence is establishing mail-order prescriptions, which may reduce the time and transportation barriers to obtaining new and refill prescriptions from a retail pharmacy.

In addition to choosing between these types of interventions, specifics about the interventions may be determined. For example, a time of day at which to make the intervention may be specified. In addition, when multiple contact methods are available, the type of contact (such as work email, home phone, etc.) may be selected along with the time of day and day of week for the intervention.

Such a system identifies which users are at risk of a gap in care and also how receptive the users will be to interventions. In this way, interventions can be targeted to have maximum impact. In some implementations, the cost or patient outcome associated with non-adherence may be taken into account so that interventions can be directed to those users where a gap in care is estimated to result in a more drastic negative outcome for the patient and/or a higher cost of treatment.

Despite these interventions, some gaps in care may still persist. Therefore, to further reduce gaps in care, the present disclosure describes a system for generating personalized healthcare plans and interventions for minimizing the gaps in care. To fully understand various aspects of the present disclosure, workings of a high volume pharmacy, including data gathering, interfacing between different parties or stakeholders, and so on are initially described with reference to FIGS. 1-3. Subsequently, an overall architecture of a system for generating personalized healthcare plans and interventions for minimizing gaps in care is described using block diagrams shown in FIGS. 4A, 4B, and 5.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, client, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other and with the benefit manager device 102 directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may also include health data about a member, such as conditions the member is diagnosed with, such as hypertension, high cholesterol, or diabetes. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy.

Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
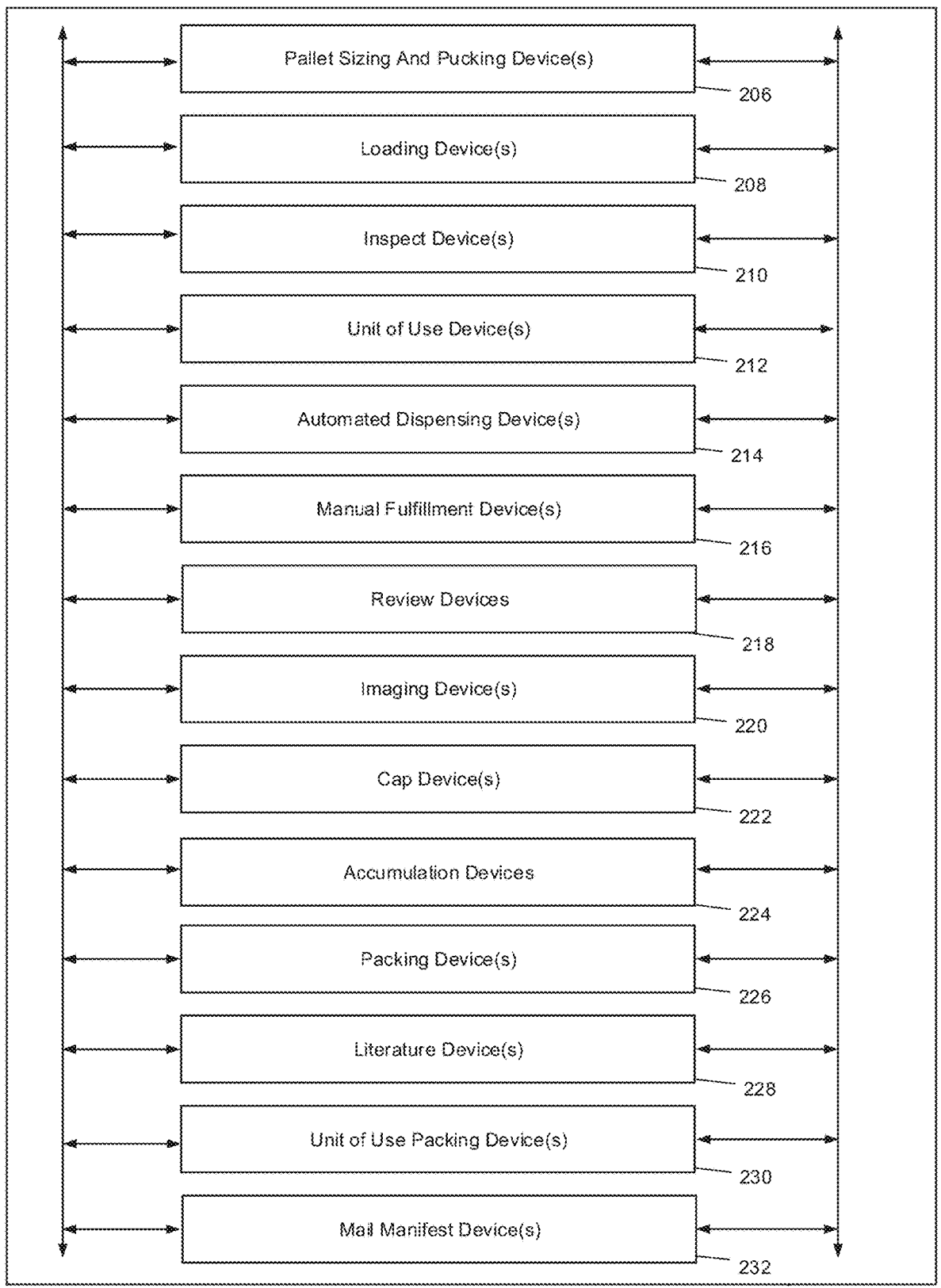
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
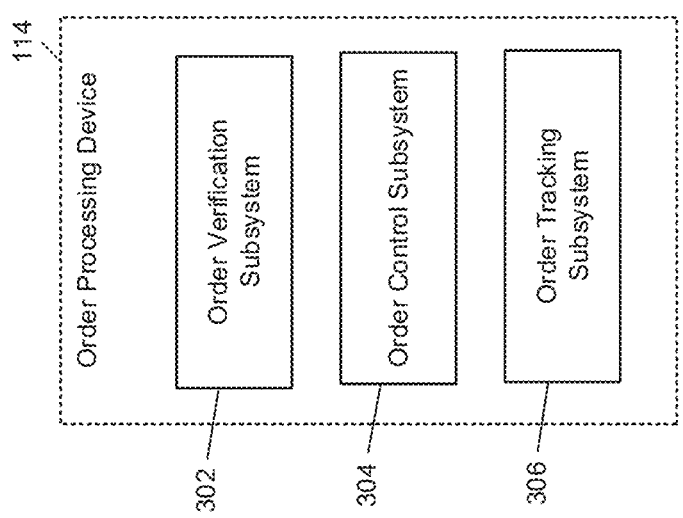
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

User-Specific Operation Set Generation

Referring back to FIG. 1, a personalized care planning system 400 (referred to as the system 400) obtains data from the storage devices 110 and from various gap-in-care engines described below with reference to FIGS. 4A, 4B, and 5. The system 400 may communicate with the user devices 108, specialist devices 404, and client devices 408 via the networks 104. The specialist devices 404 may include devices used by pharmacists and pharmacist technicians for executing interventions such as placing phone calls to users. The specialist devices 404 may also include devices used by physicians and nurses for executing other interventions. The client devices 408 may be operated by clients such as representatives and managers of health insurers. A web portal 412 may be used to provide various reports generated by the system 400 as described below. Further, the managers may use the web portal 412 to monitor the performance of the system 400. The managers may also use the web portal 412 to interact with the system 400 and to refine aspects of the system 400 to narrow the gaps in care as described below in detail.

Figure 4A:
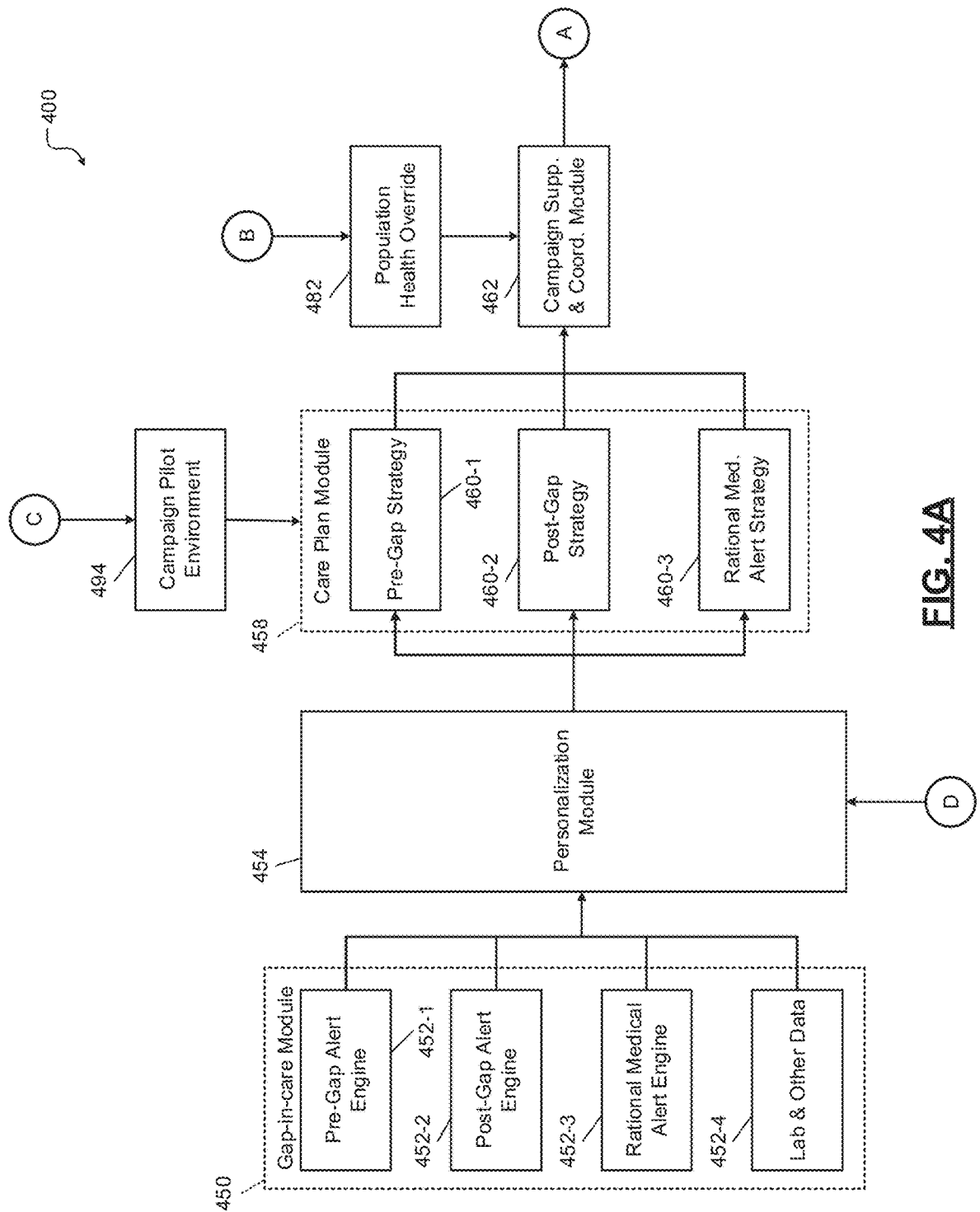
FIGS. 4A and 4B show an example of an architecture of a system for generating personalized healthcare plans and interventions for minimizing gaps in care.
Figure 4B:
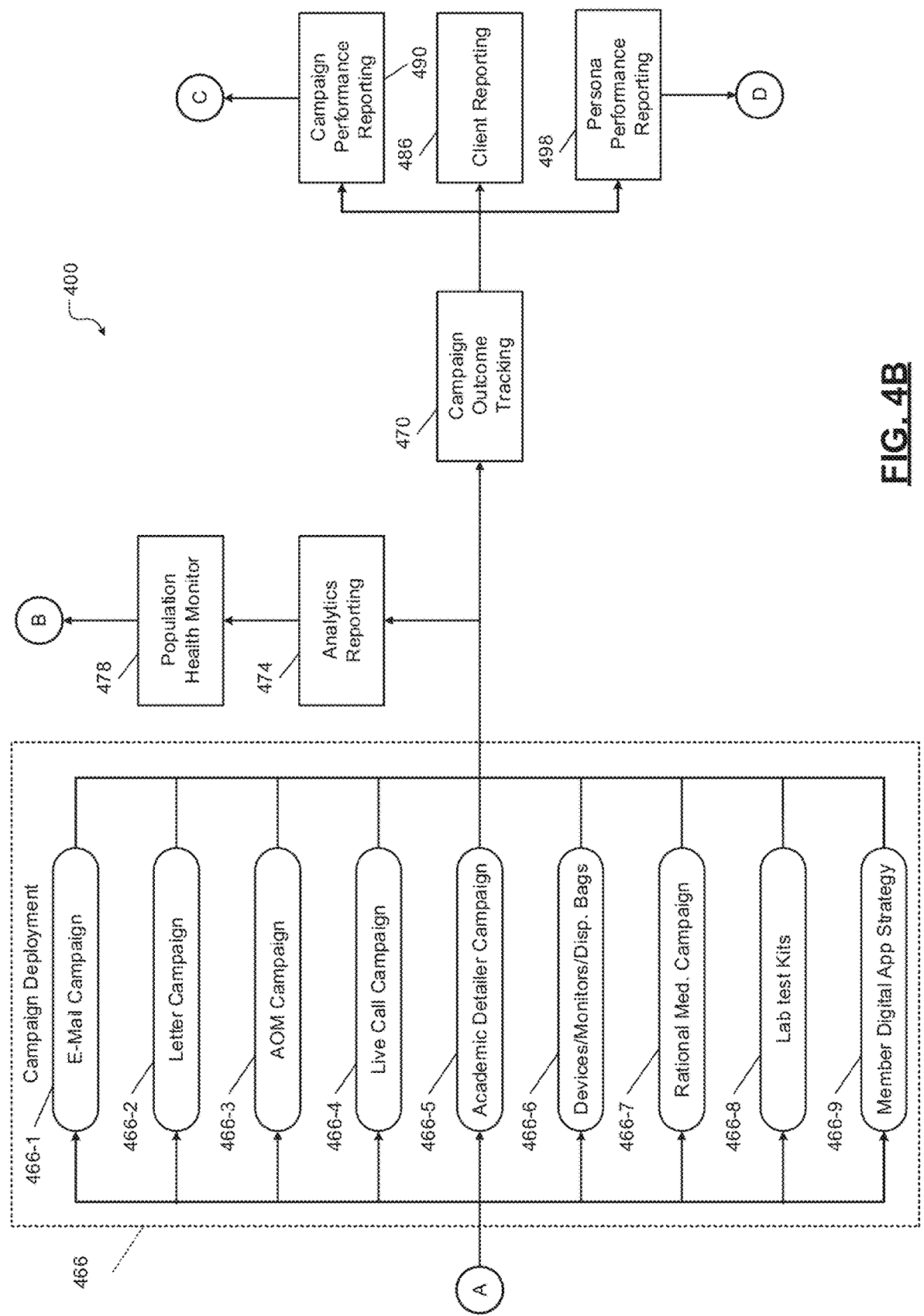

FIGS. 4A and 4B show an example of an overall architecture of the system 400. FIG. 5 shows an example of an implementation of the system 400. The system 400 provides better care for members in a personalized manner. The system 400 uses a flexible process that allows clients to modify care strategy at any time to reduce gaps in care. The system 400 provides population health managers with capabilities to override and modify care strategies. The system 400 achieves the following objectives: adherence gap prevention; faster and longer adherence gap closures; closure of other clinically valuable measures; and improvements in lab, screening, and testing among patients.

FIGS. 4A and 4B show the main components of the system 400, which include a gap-in-care module 450, a personalization module 454, a care plan module 458, a campaign suppression and coordination module 462, a set of defined campaigns 466, a campaign outcome tracking module 470, an analytics reporting module 474, a population health monitor module 478, a population health override module 482, a client reporting module 486, a campaign performance reporting module 490, a campaign pilot environment module 494, and a persona performance reporting module 498. These components or features are initially briefly described below and are subsequently described in detail with reference to FIG. 5.

Briefly, the gap-in-care module 450 includes a pre-gap alert engine 452-1, a post-gap alert engine 452-2, a rational medical alert engine 452-3, and a laboratory alert engine 452-4 that integrates other data. The engines 452-1, 452-2, 452-3, and 452-4 (collectively, engines 452) identify gaps in care and provide clinical opportunities to the personalization module 454. The personalization module 454 creates patient personas to tie to a campaign communication strategy depending on various scores of the patient.

For example, the scores include the following. A risk score indicates a patient's risk of experiencing gap in care (for example, within a predetermined time from the present, such as the next 3 months). An engagement score indicates likelihood of a patient having a positive outcome of a targeted action. A channel score indicates a patient's preference for a communication channel (e.g., email, text message, phone call, etc.). A patient's out-of-pocket (OOP) expense score indicates likelihood of a patient experiencing greater OOP cost. The OOP expense score can be used to formulate a suitable message for the patient in a selected campaign strategy so that the patient can be more responsive to a selected care plan. A physician score indicates a prediction of how successful a physician will be in closing the gap in care for a patient who does not respond well to other campaigns. A pharmacy score indicates a prediction of how successful a pharmacy will be in closing the gap in care for a patient who does not respond well to other campaigns.

The care plan module 458 creates one or more care plans for the patient based on the patient's scores. The care plans may be based on one or more of a pre-gap strategy 460-1, a post-gap strategy 460-2, and a rational medical alert strategy 460-3. Care plan creation is described in more detail with reference to FIG. 5 below.

The campaign suppression and coordination module 462 optimizes the care plans. For example, a care plan that cannot be executed (e.g., due to inadequate patient contact information, patient being a minor, etc.) may be dropped. Further, the care plans may involve a tiered strategy that provides for gradual escalation. For example, a care plan may begin by contacting a patient using the least intrusive method (such as email) and, due to lack of response from the patient, escalate to text messaging, live phone call, etc. As another example, a care plan may increase the contact frequency of a selected campaign method and decrease wait time before accelerating to the next level. This methodology is described in further detail with reference to FIG. 5 below.

The set of campaigns 466 shows various types of campaigns that can be deployed according to the care plans. For example, the set of campaigns 466 includes the following types of campaigns (the list is not exhaustive): an email campaign 466-1; a letter campaign 466-2; an automated outbound messaging (AOM) campaign 466-3; a live call campaign 466-4; an academic detailer (a pharmacist working with a physician) campaign 466-5; a campaign 466-6 that delivers devices, monitors, disposal bags, etc. that incentivize patients to comply with care plans; a rational medical campaign 466-7 (e.g., automated outreach to physicians via electronic medical records); a lab campaign 466-8 using lab test kits that assist patients to comply with care plans in lieu of lab results; and a digital campaign 466-9 leveraging a member digital app strategy, where a smartphone app with compliance-assisting capabilities is provided, which patients may find convenient to use, resulting in improved care.

The campaign outcome tracking module 470 tracks the savings and performance of the care plans and the effectiveness of the campaign strategies deployed according to the care plans. The analytics reporting module 474 tracks member targeting and campaign volume to make sure it meets clients' and products' needs and does not waste resources (such as due to unnecessary campaigning). The analytics reporting module 474 reports the performance of the care plans and the effectiveness of the campaign strategies to a population health manager. The population health monitor module 478 monitors the performance of the care plans and the effectiveness of the campaign strategies based on the analytics reporting module 474. Based on the monitoring, when it is necessary to reduce waste or to modify a care plan and/or campaign strategy to increase its effectiveness, the population health manager accesses the campaign suppression and coordination module 462 (e.g., using the web portal 412 as explained below with reference to FIG. 5). The population health manager may fine tune, modify, or override some of the features/parameters of a care plan or a campaign strategy. This aspect of the system 400 is shown as the population health override module 482.

The client reporting module 486 reports to the client the savings and performance of the care plans and the effectiveness of the campaign strategies deployed according to the care plans. The campaign performance reporting module 490 provides feedback on performance of each care plan, which is used in conjunction with the campaign pilot environment module 494 by the care plan module 458 to generate more effective care plans. The persona performance reporting module 498 provides feedback regarding performance of the personas used in the campaigns and care plans. The feedback is used by the personalization module 454 to create improved personas to tie to campaign communication strategy.

Thus, using the system 400, the personalization of patients' care is generally performed as follows. Data from multiple sources such as pharmacy claims, medical and laboratory data, and so on is collected. The data is analyzed to identify opportunities for clinical improvements in patients' healthcare. The data is input to a prediction model that helps in determining which members need a specific level of care so that a care plan can be generated for these members.

A recommendation engine uses the prediction model's output to identify the right clinical interventions for these members. The recommendation engine also provides predictions regarding how each member will engage with the interventions and which communication channel will be most effective through which the member will engage with the interventions. The interventions are then deployed through that communication channel. Notably, the interventions are focused on the patients' whole health and are not limited to pharmaceutical related outcomes but also include medical related outcomes. The interventions also include remote weight monitoring, healthy eating, and related consultations with clinicians.

Further, the system 400 can provide data regarding interventions and so on to clients (for example, health plans) via a dashboard (e.g., via the web portal 412). The clients can use the dashboard to add their own interventions to the system 400. A population health manager of each client monitors outcomes of the interventions and modifies the campaign strategy and care plans for its patient population to meet the plan goals.

In some implementations, the personalization engine's components include a gap in care model, a generalized engagement model, and a channel specific engagement model. Using these models, the personalization engine creates patient personas. For each persona, the personalization engine creates a digital care plan or a custom campaign strategy. The campaign strategy is created based on multiple scores for the patient. For example, as mentioned above, the scores can include a risk score, an engagement score, a channel score, a physician score, a pharmacy score, and so on.

The personalization and optimization of a patient's care are generally performed as follows. After identifying the opportunities for clinical improvements and creating the right persona and care plan that match a patient, a combination of campaign strategies is identified to achieve a desired outcome. There may be multiple different opportunities for clinical improvements and multiple different strategies for deploying interventions to implement those improvements. An appropriate combination of the opportunities and strategies is determined that will coordinate actions of all three participants—the physician, the pharmacy, and the patient—to achieve the desired outcome. The two components of the relevant strategy are the relevant persona and the relevant care plan. Feedback from the performance of the deployed strategy (campaign outcomes) is used to continuously refine the persona and the care plan determinations.

Care plans are generally created as follows. A clinical opportunity for a patient is identified. A persona of how the patient is likely to engage is created. A care plan involves one or more ways of communicating with the patient (e.g., phone call, text message, email, etc.) that can elicit the best response for that patient to yield the desired outcome for the clinical opportunity. Essentially, a care plan is the best likelihood of successful patient engagement.

Personas are generally created as follows. As mentioned above, multiple scores for a patient are determined using different models. For example, the scores include a risk score, an engagement score, a channel score, a physician score, a pharmacy score, etc. Each score can have a range of values (e.g., high, medium, and low). For a patient, a combination of the values of the scores is a persona.

Accordingly, for N scores, each having three possible values, theoretically there can be $3^N$ personas. Some personas may be indistinguishable from each other and therefore may have the same care plan.

The care plans are not directed solely to the consumer (patient) but are also directed to the physician and the pharmacy. That is, in some cases, depending on the scores, a patient may be able to engage with a care plan independently while, in other cases, the patient may not be able to engage with a care plan unassisted and may therefore need to be directed to a physician and/or the pharmacy to improve the patient's adherence to treatment. For example, if a patient has a high risk score, a low engagement score, and a low channel score, the care plan for such a patient may involve directing the patient to the physician. Depending on a patient's score, the care plan for the patient can be directed to the patient, the physician, the pharmacy, or any combination thereof.

Some care plans involving digital communication (e.g., text messaging, emails, automated calling, etc.) can be executed automatically. Further, some care plans can be generated and/or executed by clients. Regardless of the type of communication channel used to implement the interventions, the results (i.e., success metrics) of all interventions are digitally recorded and tracked in an automated way based on the claims filed following the interventions. In various implementations, the claims are based on prescription orders. In care plans not involving prescriptions (e.g., remote weight or diet monitoring), the outcomes or results would be based on the relevant data received from the patients after the care plan is applied to the patient. For example, a care plan may include weight monitoring, and the outcome or the result may be measured by whether the patient measured the weight as directed (e.g., daily, weekly, etc.) and whether the weight changed (decreased or increased) as desired.

Figure 5:
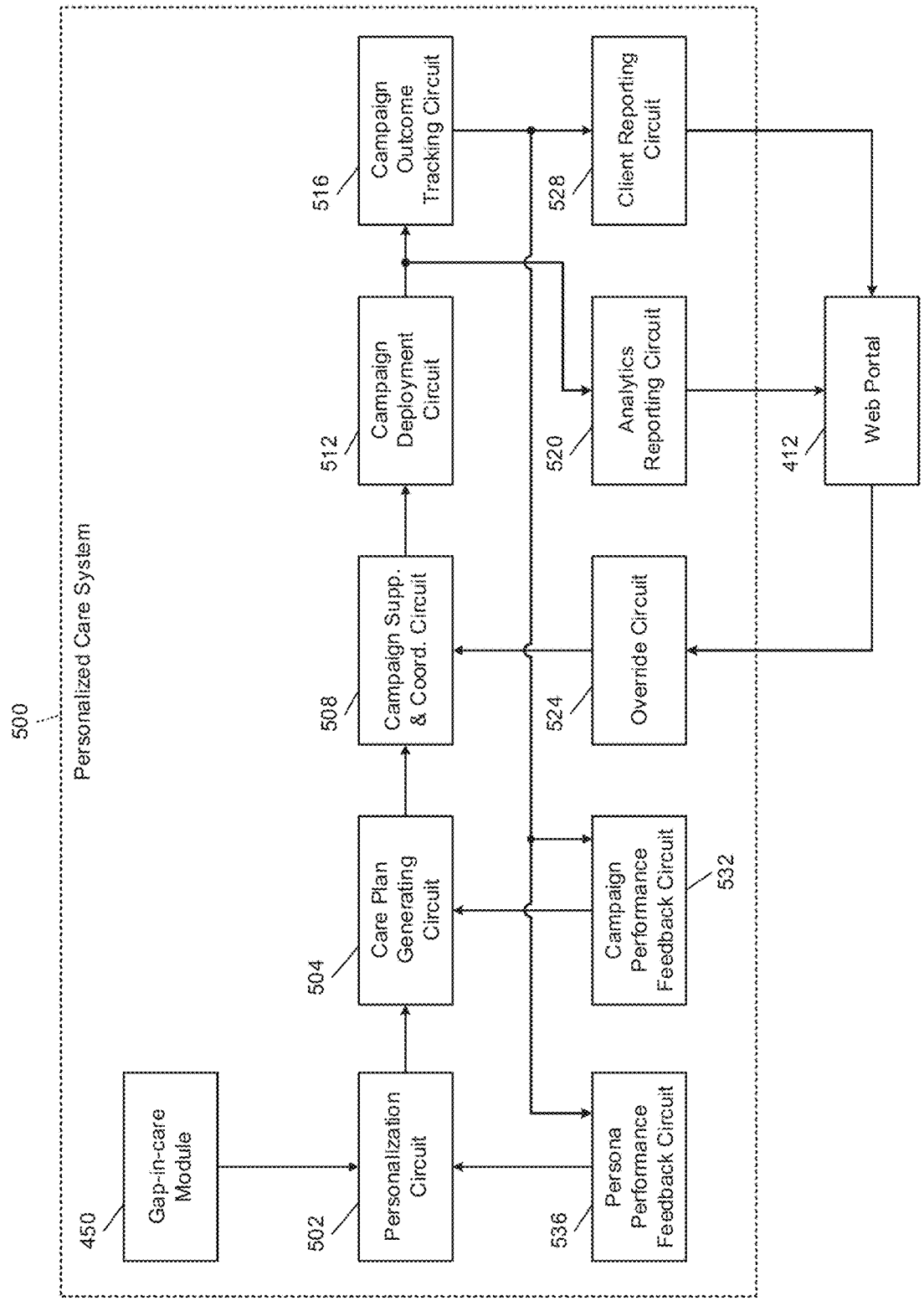
FIG. 5 is a functional block diagram of an example of the system of FIGS. 4A and 4B.

FIG. 5 shows an implementation of a personalized care system 500 in communication with the web portal 412. While the gap-in-care module 450 are shown as being a component of the personalized care system 500, the gap-in-care module 450 may be part of another system and may provide the alerts indicating gaps in care (clinical opportunities) to the personalized care system 500. The components shown in FIG. 5 may be implemented similarly to the components shown in FIGS. 4A and 4B.

The personalized care system 500 includes a personalization circuit 502, a care plan generating circuit 504, a campaign suppression and coordination circuit 508, a campaign deployment circuit 512, a campaign outcome tracking circuit 516, an analytics reporting circuit 520, an override circuit 524, a client reporting circuit 528, a campaign performance feedback circuit 532, and a persona performance feedback circuit 536.

In FIG. 5, while constituents of some of the components, which are shown in FIGS. 4A and 4B, are not shown, it is understood that these constituents may be present in these components in FIG. 5. These constituents are referenced during the description of the respective components below.

Various clinical rules-based engines (e.g., from the gap-in-care module 450) generate alerts indicating possible or actual gaps in care (also called clinical opportunities). For example, a pre-gap alert engine (e.g., element 452-1 shown in FIG. 4A) can provide alerts indicating possible gaps in care that may occur. A post-gap alert engine (e.g., element 452-2 shown in FIG. 4A) can provide alerts indicating actual gaps in care that already exist and that are not closed by campaign strategies developed based on the alerts provided by the pre-gap alert engine. A rational medical alert engine (e.g., element 452-3 shown in FIG. 4A) can provide alerts indicating gaps in care relating to errors in medication that put patient's health at risk. Finally, a lab alert engine (e.g., element 452-4 shown in FIG. 4A) can provide alerts indicating gaps in care based on laboratory and other data. These alert engines provide data regarding clinical opportunities for making improvements in patients' healthcare. These clinical opportunities are input to the personalization engine (e.g., the personalization circuit 502).

The personalization engine (e.g., the personalization circuit 502) creates a persona for the patient to tie to a campaign communication strategy. The personalization engine matches a clinical opportunity for a patient to a particular persona. Based on scores such as the risk score, engagement score, and channel score for the patient, the personalization engine determines the right intervention method (directed to patient, physician, or pharmacy). Based on the patient's out of pocket (OOP) cost score, the personalization engine determines the right type of message to convey to the patient along with the intervention. Based on the physician score and the pharmacy score for the patient, together with the patient's risk score, engagement score, and channel score, the personalization engine determines whether the intervention method should be directed to a physician or a pharmacy.

Based on the type of alert engine that provides the clinical opportunity and the patient persona, a custom campaign strategy or care plan (e.g., a pre-gap, post-gap, or rational medical care plan) is created for the patient by the care plan generating circuit 504. The care plan is deployed by the campaign deployment circuit 512 following optimization and suppression performed by the campaign suppression and coordination circuit 508.

Multiple care plans may be created for a patient. Depending on the client's performance guarantee and availability of resources, an optimization engine (also called campaign coordination engine and shown as the campaign suppression and coordination circuit 508) optimizes the care plans for the patient. Optimization involves coordinating the care plans to yield the desired outcome.

The optimized care plans are then executed by the campaign deployment circuit 512 by using one or more campaign strategies recommended by the optimized care plans. For example, the campaign strategies may include sending emails, letters, automated outbound messaging (AOM), and/or live calling. For example, these campaign strategies may be used to escalate patient adherence and compliance with the optimized care plans.

Additional campaign strategies for improving patient care may be recommended by the optimized care plans. For example, the additional campaign strategies may involve an academic detailer, who is a pharmacist advising a physician regarding what gaps in care exist for patients so that the physician can improve patient care accordingly. In other examples, devices, monitors, and/or disposal bags may be sent to the patient to assist and encourage the patient in complying with the optimized care plan. A rational medical campaign may involve automated outreach to the physician. Lab test kits may be sent to the patient, again to motivate the patient to perform the necessary tests at home, which obviates a lab visit, and return the test results as part of the optimized care plan. Further, a smartphone app may be provided to the patient to make it easy for the patient to comply with the optimized care plan (e.g., ease of ordering prescription, keeping doctor's appointments, providing test data and vital statistics etc. using the app). This list of campaign strategies is not exhaustive. Other campaign strategies are contemplated.

Further, the optimization engine (e.g., the campaign suppression and coordination circuit 508) may also suppress (that is, not implement) a care plan if, for example, the care plan does not meet privacy or legal requirements (e.g., calling a minor may be avoided), the patient's contact information on file is incorrect, etc. If one type of contact information is unavailable, another type of contact information is selected to initiate contact.

The volume and outcomes of the various campaigns are tracked per patient by the campaign outcome tracking circuit 516. Further, the analytics reporting circuit 520 may report member targeting and campaign volume onto a dashboard on the web portal 412. Based on the tracking and reporting, a client's population health manager may determine that one or more campaigns needs to be modified (e.g., calling the patient earlier than recommended by the optimized care plan, discarding an email channel altogether, etc.). Accordingly, the population health manager may override some of the features recommended by the optimized care plan and modify the optimized care plan. The population health manager may perform the tracking and modifications using the dashboard provided by the personalized care system 500 via the web portal 412. The override circuit 524 and the campaign suppression and coordination circuit 508 may carry out the modifications desired by and received from the population health manager via the web portal 412.

A database of the outcomes of campaigns is maintained by the campaign outcome tracking circuit 516. Success rates of the campaigns and savings from the campaigns are tracked using the database. Based on the database, three types of reports may be generated: a campaign performance report, a client report, and a persona performance report. The client report is generated by the client reporting circuit 528 and includes overall savings resulting from the campaigns for each client.

The campaign performance report is generated by the campaign performance feedback circuit 532 for each care plan and includes a comparison of actual performance of a care plan to a suggested or expected performance (success measure) for the care plan. The campaign performance report may also include a comparison with another care plan or a control group of care plans or a pilot campaign environment. The comparison is made to determine which care plan is yielding the best clinical outcome for a given clinical opportunity. The knowledge gained from the comparisons is used as feedback to improve creation of care plans by the care plan generating circuit 504.

The persona performance report is generated by the persona performance feedback circuit 536 and indicates how the persona created by the personalization engine performed. Based on the feedback about the performance of the persona, the personalization engine (e.g., the personalized care system 500) can refine the creation of subsequent personas.

Flowchart

Figure 6:
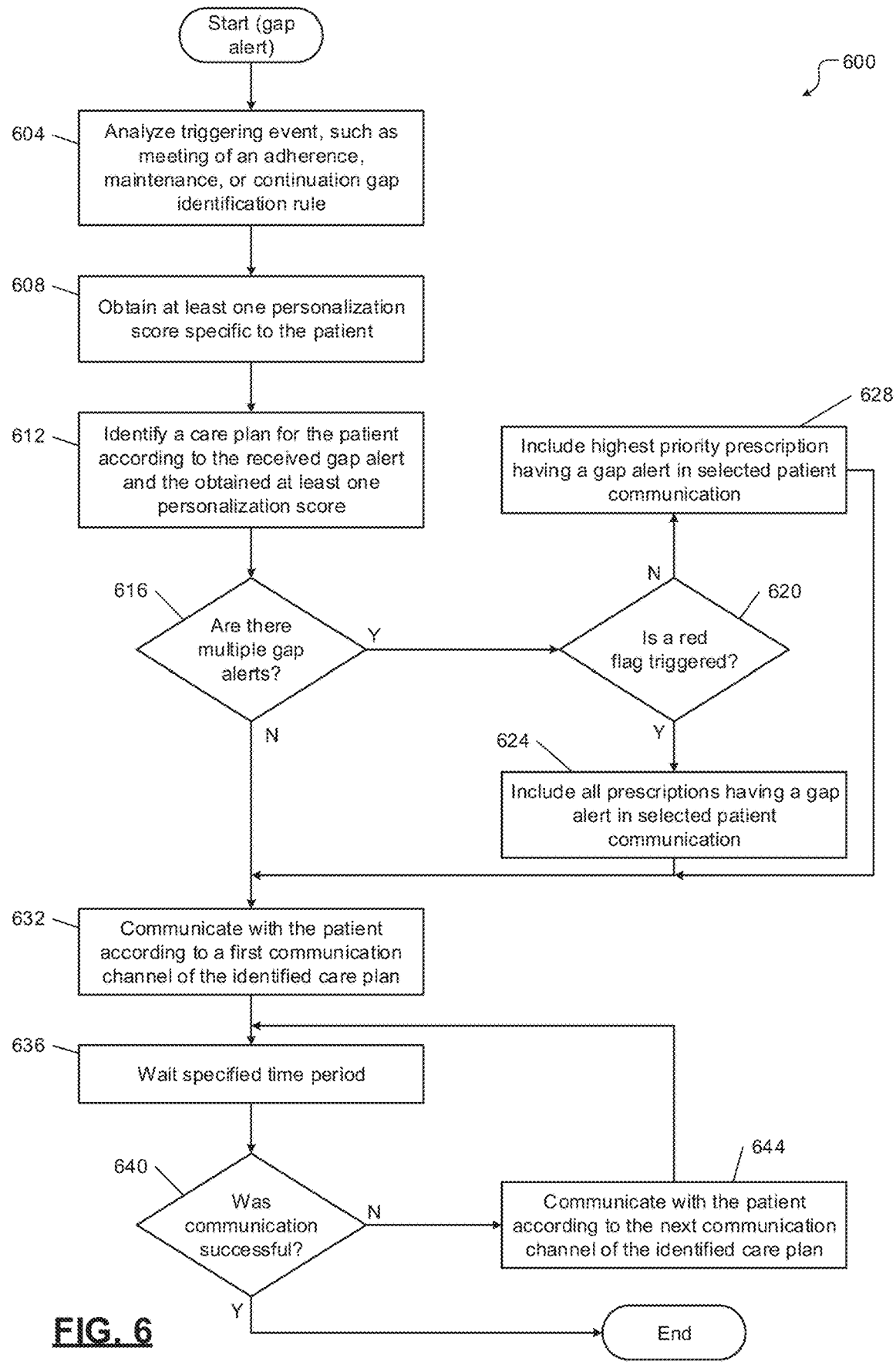
FIG. 6 is a flowchart depicting an example method of executing a personalized healthcare plan and intervention for minimizing gaps in care.

FIG. 6 is a flowchart of an example method 600 of generating and executing an ordered operation set for a patient. The ordered operation set may specify an ordered sequence of interventions. Each intervention may include one or more communications. The ordered operation set is personalized to the patient and configured to minimize gaps in care for patient. Although the method 600 is in the context of the personalized care system 500, the method 600 may be implemented by other devices and/or systems.

In FIG. 6, control begins at 604 in response to receiving an automated gap alert for a patient. At 604, control analyzes the triggering event for the gap alert. For example, automated triggering events may occur based on an adherence gap identification rule, a maintenance gap identification rule, or a continuation gap identification rule. One example of an adherence gap identification rule is that a patient has medication on hand below a specified threshold (e.g., below eighty percent, etc.). For example, if the number of refills obtained by the patient indicate that the patient has less than eighty percent of the amount of medication that the patient should have at the current time point of the treatment or prescription plan, an adherence gap identification rule may be triggered to indicate that the patient is not sufficiently adhering to the treatment or prescription plan.

The gap identification rule may be automatically triggered in response to monitoring of a patient's refill count, etc. For example, records of a patient's obtained refills may be periodically compared to a refill schedule of a treatment or prescription plan for the patient, to determine whether the patient is adhering to the refill schedule. The gap alert, gap identification, automated rules, etc., may be performed by the gap-in-care module 450.

A maintenance gap identification may occur when the patient meets the criteria, but is late to refill a prescription according to the refill schedule. For example, a patient may have a history of following the refill schedule for one or more prior refills, but the patient may be late to obtain a most recent refill. If the patient is late to refill by more than a specified delay period (e.g., more than zero days, more than one week, more than two weeks, more than thirty days, etc.), the maintenance gap identification rule may be triggered automatically based on one or more rules that compare the patient's refill history, or missed refill time point, to a refill schedule for the patient.

A continuance gap identification may occur for brand new prescription refills where the personalized care system 500 does not have any data yet about a patient's prior adherence or non-adherence to a refill schedule (for example, because the patient has not yet established any refill history). For example, if a patient is prescribed a new prescription for the first time, or for the first time in the last year, etc., and is late to fill the first prescription, a continuance gap identification rule may be triggered. Continuance gaps may be identified separately from adherence gaps, or maintenance gaps, because patients may have a higher risk of a gap in care when initially starting a new prescription or obtaining a first refill of a new prescription (as compared to a patient with a longer refill history). Although FIG. 6 illustrates three types of gap identifications, in various implementations other rules, alerts, etc., may be used to trigger identified gaps in care.

At 608, control obtains at least one personalization score that is specific to the patient. For example, the personalization module 454 may determine a risk score specific to the patient, an engagement score specific to the patient, a channel score specific to the patient, an out-of-pocket (OOP) expense score specific to the patient, a physician score specific to the patient, a pharmacy score specific to the patient, etc. These scores may be stored in a personalization score database of patients having prescriptions and/or refill schedules. The scores may be obtained and/or updated by periodically accessing databases for patient information, supplying patenting details to one or more machine learning models used to calculate and/or predict patient scores based on patient information, etc.

Control identifies a care plan for the patient at 612, according to the received gap alert and the obtained at least one personalization score. For example, the care plan may be identified by the care plan module 458. Combining the personalization score(s) that are specific to the patient with the identified gap in care, allows for selection of a more specific and effective care plan to target the patient and increase the likelihood of intervening to minimize the gap in care.

Utilizing the risk scores, engagement scores, communication channel scores, etc., that are specific to the patient provides further insight into the type of outreach that should be used for the specific patient in order to minimize the gap in care most effectively, and improves results as compared to merely identifying a gap and then using the same outreach plan for every patient. For example, the additional personalization scores that are specific to the patient may suggest the best individual to reach out to (e.g., a call to the patient directly, outreach from a physician or pharmacist, etc.), and may suggest the best communication channel to reach the patient (e.g., an automated call, an email, a live call, a text message, etc.).

At 616, control determines whether multiple gap alerts exist. For example, a patient may have multiple different prescriptions for different treatment conditions that are late to refill, a treatment plan for a single condition may include multiple drugs that should be refilled at the same time, etc. If there are multiple gap alerts, control proceeds to 620 to determine whether a red flag condition has been triggered. A red flag condition may occur when there are multiple gap alerts above a specified threshold (e.g., at least two gap alerts, at least three gap alerts, etc.).

As an example, if three different gap alerts exist for a patient because they have three different prescriptions that are late to fill, a red flag condition may be triggered. In that case, control proceeds to 624 to include all prescriptions having the gap alerts in the selected patient communication. If the communication is a live call, the caller may discuss all three of the late prescription refills with the patient during the call, in an attempt to minimize the gap for all three prescription refills.

If a red flag condition is not triggered at 620, control proceeds to 628 to include a highest priority prescription having a gap alert in the selected patient communication. For example, for a diabetes treatment plan, a variety of different drugs may be prescribed, which may each have different priorities. An example priority list may be, in order, metformin, SGLT2 inhibitors, DDP-4 inhibitors, oral insulin secretagogues, thiazolidinediones, basal insulin, incretin mimetics, premix insulin, and lastly alpha glucosidase inhibitors. In this example, if a patient has a gap alert for both metformin and DDP-4 inhibitors, the selected communication may focus on only the metformin in an attempt to minimize the gap for the metformin as a highest priority (e.g., an email to the patient may only refer to the metformin gap, a call to the patient may only discuss the metformin gap, etc.).

Once the prescription(s) for the communication are selected at 624 or 628, or if there are not multiple gap alerts at 616, control proceeds to 632 to communicate with the patient according to a first communication channel of the identified care plan. For example, the identified care plan may specify a first communication channel as sending an email to the patient to remind them about refilling the prescription. The communication may be performed according to the set of campaigns 466. For example, a system encompassing the set of campaigns 466 may include an automated email system, an automatic phone dialer for connecting clinicians to patients, an automatic phone system for leaving messages, an interactive voice recognition engine for engaging patients, etc.

At 636, control waits a specified time period after the first communication, and then determines whether the communication was successful at 640. For example, after sending out an email reminder to refill the prescription, control may wait three days, a week, etc., to see if the patient refills the prescription. If so, the gap has been successfully minimized and control can end the process.

If the communication did not result in a successful refill at 640, control continues to 644. At 644, control communicates with the patient according to the next communication channel of the identified care plan. For example, if the patient does not refill the prescription within a week of the email communication, control may move on to an automated call communication, a text message communication, etc., according to the care plan communication priority, instead of simply repeating additional email communications.

If the patient does not refill the prescription within the specified time period after the second communication, control may proceed to further communication types according to the identified care plan. For example, if the patient does not refill the prescription within a week of the text message or automated call communication, control may proceed to communicate via a live call, reach out to the patient's physician to contact the patient directly, etc. The levels of communication may be specified at the outset in the identified care plan, and control may automatically proceed through the types of communication according to specified rules (e.g., moving from one communication type to the next after a specified time period following a prior unsuccessful communication, after a specified number of attempts with a prior unsuccessful communication, etc.). This approach may allow for less intrusive and less time- and resource-intensive outreach attempts initially, with the communications becoming more involved over time if the initial attempts are unsuccessful. This progression is part of an ordered operation set, not a manual review by a clinician.

In various implementations, the system 400 or the personalized care system 500 may determine whether the patient is a good candidate for specialized outreach such as sending a smart glucose meter to the patient, sending a lab test kit to the patient, providing a mobile tracking application to the patient, etc. These approaches may be automatically determined according to rules that incorporate the personalization scores of the patient.

A user interface may be provided that allows a patient to access aspects of the system 400 or the personalized care system 500, allows health care providers to access the system, etc. For example, the patients, health care providers, etc., may be able to access the system via the Internet, using sufficient security measures such as two-factor authentication, etc.

As discussed above, in various implementations a population manager, administrator, etc., may be able to modify the health stored care plans, automated rules, gap identification triggers, etc. For example, outcomes of the health care plans communications may be reviewed in a closed-loop feedback system to determine whether or not they are successful (e.g., based on the level of successful prescription refill outcomes, the amount of time taken to obtain a successful prescription refill outcome, etc.). The outcome-based modifications may be performed automatically according to one or more rules, in order to modify the types of communications included in care plans, the priority and timing of communication types in care plans, etc.

In various implementations, pre-gap alerts may be generated and monitored in order to communicate with patients prior to a scheduled refill. The pre-gap alerts may be used as reminders for the patients in an attempt to avoid a potential gap in care. The pre-gap communications may be sent to patients who are new to a prescription, prior to any non-adherence occurring.

Conclusion

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized method comprising:
receiving (i) a user record including one or more authorized instructions and (ii) an event schedule corresponding to one of the one or more authorized instructions, wherein each authorized instruction includes authorization from a third party selected by a user associated with the user record;
determining whether the user record fails to satisfy the event schedule, wherein the failure is indicative of a maintenance failure associated with the user;
in response to the user record failing to satisfy the event schedule, obtaining a set of personalization scores for the user generated by a set of predictive models, wherein each predictive model is configured to receive user data from a plurality of networked devices and generate a personalization score dependent on the user data received as input to the respective model, wherein each personalization score indicates a user-related likelihood, and wherein the set of personalization scores includes:
a first score characterizing a behavior of the user;
a second score characterizing an affinity of the user to a communication channel for communicating with the user; and
a third score characterizing a receptiveness of the user to one or more maintenance providers;
generating an aggregate score representing the user based on a combination of the one or more personalization scores from the set of personalization scores that are specific to the user;
selecting a set of communication protocols based on the one or more personalization scores, wherein each communication protocol includes a mode of communication with the user either directly or through at least one third party;
generating a compliance plan for reducing the maintenance failure, wherein the compliance plan includes a hierarchy of communication protocols from the set of communication protocols based on the aggregate score, and wherein the compliance plan includes a set of rule-based conditions that automatically trigger a respective communication protocol that corresponds to a level of the hierarchy; and
automatically deploying the care compliance plan by:
generating a first compliance message with a first communication protocol that corresponds to a first level of the hierarchy associated with the compliance plan;
determining that the maintenance failure persists for a threshold period of time after communication of the first compliance message; and
generating a second compliance message with a second communication protocol that corresponds to a second level of the hierarchy associated with the compliance plan, wherein the second level demands greater communication resources than the first level.

2. The computerized method of claim 1, wherein:
the first score indicates at least one of a risk of the user having the maintenance failure and a likelihood of the user having a positive outcome of a targeted action aimed at reducing the maintenance failure; and
the third score indicates at least one of an ability of a physician to reduce the maintenance failure and an ability of a pharmacist to reduce the maintenance failure.

3. The computerized method of claim 2, wherein the set of communication protocols are selected according to at least two of the first score, the second score, and the third score.

4. The computerized method of claim 1, wherein automatically deploying the compliance plan further: comprises monitoring whether the maintenance failure persists at one or more monitoring increments dictated by the compliance plan.

5. The computerized method of claim 1, wherein determining whether the user record fails to satisfy the event schedule includes determining whether a physical inventory possessed by the user and authorized by the one of the one or more authorized instructions falls below a specified threshold.

6. The computerized method of claim 1, wherein a respective communication protocol of the set corresponds to at least one of an email campaign, a letter campaign, an automated outbound messaging (AOM) campaign, a live call campaign, an academic detailer campaign, a medical device or monitor campaign, a rational medical campaign, a lab test kit campaign, and a member digital application campaign.

7. The computerized method of claim 1, wherein:
the maintenance failure includes a missed prescription drug refill; and
the hierarchy of communication protocols includes escalating communicating protocols promoting the fulfillment of the missed prescription drug refill.

8. The computerized method of claim 1, further comprising:
receiving a second user record and a second event schedule corresponding to the one or more authorized instructions; and determining whether the second user record for the user fails to satisfy the second event schedule,
wherein the failure is indicative of failing to comply with an authorized instruction associated with the second event schedule.

9. The computerized method of claim 8, wherein selecting the set of communication protocols is further based on both the maintenance failure and the failure indicative of failing to comply with the authorized instruction associated with the second event schedule.

10. The computerized method of claim 8, wherein generating the compliance plan includes:
determining which of the maintenance failure or the failure indicative of failing to comply with the authorized instruction has a highest priority; and
generating the hierarchy of communication protocols according to the highest priority.

11. A computer system comprising:
memory configured to store computer-executable instructions and a personalization database including one or more personalization scores that are specific to a user; and
at least one processor configured to execute the instructions, wherein the instructions include:
receiving (i) a user record including one or more authorized instructions and (ii) an event schedule corresponding to one of the one or more of the authorized instructions, wherein each authorized instruction includes authorization from a third party selected by a user associated with the user record;
determining whether the user record fails to satisfy the event schedule indicating maintenance failure associated with the user;
in response to the user record failing to satisfy the event schedule, obtaining a set of personalization scores for the user generated by a set of predictive models, wherein each predictive model is configured to receive user data from a plurality of networked devices and generate a personalization score dependent on the user data received as input to the respective model, wherein each personalization score indicates a user-related likelihood, and wherein the set of personalization scores includes:
a first score characterizing a behavior of the user;
a second score characterizing an affinity of the user to a communication channel for communicating with the user; and
a third score characterizing a receptiveness of the user to one or more maintenance providers;
generating an aggregate score representing the user based on a combination of the one or more personalization scores that are specific to the user;
selecting a set of communication protocols based on the one or more personalization scores, wherein each communication protocol includes a mode of communication with the user either directly or through at least one third party;
generating a compliance plan for reducing the maintenance failure, wherein the compliance plan includes a hierarchy of communication protocols from the set of communication protocols based on the aggregate score, and wherein the compliance plan includes a set of rule-based conditions that automatically trigger a respective communication protocol that corresponds to a level of the hierarchy; and
automatically deploying the care compliance plan by:
generating a first compliance message with a first communication protocol that corresponds to a first level of the hierarchy associated with the compliance plan;
identifying that the maintenance failure persists for a period of time after the communication of the first compliance message;
determining that the period of time satisfies a rule-based condition for a second level of the hierarchy; and
generating a second compliance message with a second communication protocol that corresponds to the second level of the hierarchy associated with the compliance plan, wherein the second level demands greater communication resources than the first level.

12. The computer system of claim 11, wherein:
the first score indicates at least one of a risk of the user having the maintenance failure and a likelihood of the user having a positive outcome of a targeted action aimed at reducing the maintenance failure; and
the third score indicates at least one of an ability of a physician to reduce the maintenance failure and an ability of a pharmacist to reduce the maintenance failure.

13. The computer system of claim 12, wherein the set of communication protocols are selected according to at least two of the first score, the second score, and the third score.

14. The computer system of claim 11, wherein automatically deploying the compliance plan further includes monitoring whether the maintenance failure persists at one or more monitoring increments dictated by the compliance plan.

15. The computer system of claim 11, wherein determining whether the user record fails to satisfy the event schedule includes determining whether a physical inventory possessed by the user and authorized by the one of the one or more authorized instructions falls below a specified threshold.

16. The computer system of claim 11, wherein a respective communication protocol of the set corresponds to at least one of an email campaign, a letter campaign, an automated outbound messaging (AOM) campaign, a live call campaign, an academic detailer campaign, a medical device or monitor campaign, a rational medical campaign, a lab test kit campaign, and a member digital application campaign.

17. The computer system of claim 11, wherein the instructions include:
receiving a second user record and a second event schedule corresponding to the one or more authorized instructions; and
determining whether the second user record for the user fails to satisfy the second event schedule,
wherein the failure to satisfy the second event schedule is indicative of failing to comply with an authorized instruction associated with the second event schedule.

18. The computer system of claim 17, wherein generating the compliance plan includes:
determining which of the maintenance failure or the failure indicative of failing to comply with the authorized instruction has a highest priority; and
generating the hierarchy of communication protocols according to the highest priority.

* * * * *

UNITED STATES PATENT AND TRADEMARK OFFICE
CERTIFICATE OF CORRECTION

PATENT NO. : 11,521,750 B1
APPLICATION NO. : 16/930822
DATED : December 6, 2022
INVENTOR(S) : Mark D. Wong et al.

It is certified that error appears in the above-identified patent and that said Letters Patent is hereby corrected as shown below:

In the Claims

In Claim 1, Column 28, Line 12, prior to the term compliance delete "care"
In Claim 11, Column 29, Line 66, prior to the term compliance delete "care"

Signed and Sealed this
Second Day of May, 2023

Katherine Kelly Vidal
*Director of the United States Patent and Trademark Office*